(12) United States Patent
Huynh et al.

(10) Patent No.: US 11,185,493 B1
(45) Date of Patent: Nov. 30, 2021

(54) BETEL LEAF EXTRACT COMPOSITION HAS BACTERICIDAL AND ANTIVIRAL PROPERTIES AND METHOD OF MANUFACTURING THE SAME

(71) Applicant: Nam Linh Huynh, Escondido, CA (US)

(72) Inventors: Tran Ky Huynh, Ho Chi Minh (VN); Nam Linh Huynh, Escondido, CA (US)

(73) Assignee: Tran Ky Huynh, Ho Chi Minh (VN)

( * ) Notice: Subject to any disclaimer, the term of this patent is extended or adjusted under 35 U.S.C. 154(b) by 0 days.

(21) Appl. No.: 17/305,054

(22) Filed: Jun. 29, 2021

(51) Int. Cl.
| | |
|---|---|
| *A61K 36/00* | (2006.01) |
| *A61K 8/9789* | (2017.01) |
| *A61K 8/35* | (2006.01) |
| *A61K 8/31* | (2006.01) |
| *A61Q 17/00* | (2006.01) |
| *A61K 8/34* | (2006.01) |
| *A61Q 19/00* | (2006.01) |

(52) U.S. Cl.
CPC .............. *A61K 8/9789* (2017.08); *A61K 8/31* (2013.01); *A61K 8/347* (2013.01); *A61K 8/355* (2013.01); *A61Q 17/005* (2013.01); *A61K 2800/805* (2013.01); *A61Q 19/00* (2013.01)

(58) Field of Classification Search
CPC .................................................... A61Q 17/005
See application file for complete search history.

*Primary Examiner* — Qiuwen Mi

(57) ABSTRACT

A bactericidal, antiviral composition including betel leaf extracts/essential oils in combination with at least two active ingredients plant extracts, a 4-allylpyrocatechol (APC) ingredient, a camphor ingredient, a water paraffin ingredient, an alcohol ingredient, other ingredients, and a water ingredient. The process of manufacturing the bactericidal, and antiviral composition simply, mixing the ingredients to create a homogenous mixture by predetermined percentage by weight of each ingredient.

6 Claims, 2 Drawing Sheets

BETEL LEAF EXTRACT COMPOSITION HAS BACTERICIDAL AND ANTIVIRAL PROPERTIES AND METHOD OF MANUFACTURING THE SAME

FIELD OF THE INVENTION

The present invention relates generally to bactericidal, deodorant, and virus resistance solutions. In particular, the present invention relates to a virus inactivating agent which is prepared from plant extracts derives from a plant and a multipurpose composition that can be used not only to be applied directly on the skin/palate/nose or on the outer surface of any product requiring antibacterial, or antiviral; but also as aroma therapeutic products, and medicinal products. More specifically, the present invention relates to betel leaf extract composition has bactericidal and antiviral properties and method of manufacturing the same.

BACKGROUND ART

According to 2016 research, essential oils are effective against a wide range of pathogens. Essential oils are considered to be potent against a diverse range of pathogens. Essential oils may disrupt the cell membrane of the targeted pathogens by increasing membrane permeability, inducing leakage of vital intracellular constituents, and interrupting the cellular metabolism and enzyme kinetics of the targeted pathogens. Medicinal and aromatic plants (MAPs) constitute a large part of natural flora and are considered an important resource in various fields such as the pharmaceutical, flavor and fragrance, perfumery, and cosmetic industries. Essential oils have great potential in the field of biomedicine as they effectively destroy several bacterial, fungal, and viral pathogens. The presence of different types of aldehydes, phenolics, terpenes, and other antimicrobial compounds means that the essential oils are effective against a diverse range of pathogens. The reactivity of essential oil depends upon the nature, composition, and orientation of its functional groups. The antimicrobial effects of essential oils and their chemical constituents have been recognized by several researchers and have shown the effects of any two or more components of the essential oil against other pathogens in humans.

More recently, the prevalence of antimicrobial drug resistance has prompted researchers to discover novel antimicrobial lead molecules to treat various human pathogens. Some of the presently available synthetic drugs fail to inhibit many pathogenic microbes. In addition, the use of synthetic chemicals for the control of pathogenic microorganisms is limited because of their carcinogenic effects, acute toxicity, and environmental hazard potential. In this regard, the exploitation of essential oils to control epidemic multidrug-resistant pathogenic microorganisms can be useful to combat various infectious diseases.

Furthermore, the stereochemical properties of essential oils can vary and depend upon the method of extraction. However, extraction products may also vary qualitatively and quantitatively in their composition. Although essential oils can be recovered using fermentation, extraction, or effleurage processes, commercial production is preferably achieved by the steam distillation process. Besides, although the use of chemical disinfectants can effectively kill bacteria and viruses in the air, cause residual problems, be dangerous, the potential for both humans and the environment. Disinfectants containing chlorine or peroxide have certain toxicity and strong irritant properties, are easy to damage skin tissues, a respiratory system with long-term use, and can cause environmental pollution during production and use of the above disinfectants.

According to research documents, the betel leaf extract contains about 15 to 40 compounds. Depending on species, or different geographical regions, the betel leaf extract/essential oil includes the following 9 groups of substances: monoterpenes (such as terpinene, pinene, limonene, thujene, camphene, etc.), sesquiterpenes (such as cadinene, elemene, caryophyllene, cubebene, etc.), alcohols (linalol, terpineol, cadinol, etc.), aldehydes (such as decanal, etc.), acids (such as palmitic acid, etc.), oxides (such as Eucalyptol, etc.), phenols (such as eugenol, chavibetol, chavicol, etc.), phenolic ethers (such as methyl eugenol) and esters (eugenol acetate, chavibetol acetate, etc.). The main components of betel leaf extract/essential oil including phenolic compounds and derivatives (eugenol, chavibetol, eugenol acetate, chavibetol acetate, 4-allylpyrocatechol diacetate, 4-allylpyrocatechol) account for a high proportion of about 25%-60% by weight. Accordingly, research show that the betel leaf extract/essential oil have inhibitory activity, killing viruses, bacteria, fungi and protozoa.

According to CN patent application No. CN112616861, the invention refers to a novel coronavirus disinfectant prepared from natural plant extract essential oil and application thereof. The disinfectant is prepared from geranium oil, cedar leaf oil, rosemary oil, neroli essential oil, and sage oil serving as raw materials. The novel coronavirus disinfectant prepared from the natural plant extract essential oil has an obvious effect on inactivating novel coronavirus SARS-CoV-2.

According to JP patent application No. JP2002212086, the invention refers to a new *Piper betle* L. extract which has excellent antibacterial and deodorizing activities in a low concentration against nasty smells and stinks caused by the proliferation of harmful microorganisms, is not oxidized to exhibit a brown color in a filtration process and during storage, and does not cause the deterioration of the activities.

According to CN Patent No. CN104666171 issued on Nov. 21, 2017, the invention refers to anti-bacterial hand lotion and preparation method thereof, the anti-bacterial hand lotion is made up of the component of following weight percentage: 0.1-0.2% disodium ethylene diamine tetraacetate, 8-10% sodium sulfate of polyethenoxy ether of fatty alcohol, 2.3-2.5% sodium n-alkylbenzenesulfonate salt, 1.0-1.2% lanolin, 1.5-2.0% cocoanut fatty acid diethanolamide, 7-8% Cocoamidopropyl betaine, 3-5% glycerine, 1.5-2.5% sodium chloride, 0.5-1.0% betel volatile oil, 0-0.003% pigment, surplus is water.

The above inventions meet the specific purposes and requirements of a technical solution. However, the disclosure of the invention does not address the adjustment of the technical parameters in the process of preparing raw materials (betel leaves) before performing the extraction. More especially for patent number CN112616861 revealing a coronavirus disinfectant, in which the essential oil extract component does not include betel leaf extract. In addition, each application product from betel leaf extract is very diverse, but only the method of use is limited to each respective application.

Therefore, it is necessary to create a betel leaf extract composition that has bactericidal and antiviral properties, multi-purpose, effective, safe, no pollution to the environment, and at the same time prevent the resistance of harmful microorganisms.

Furthermore, it is necessary to create a betel leaf extract composition has bactericidal and antiviral properties in a short time, not only to be used topically/sprayed/sprayed directly on the skin/palate/nose or on the outer surface of any product requiring antibacterial, or antiviral; but also strengthen the body's immune system, more specifically coronavirus prevention and health safety for all ages, especially the elderly and children.

Finally, what is need to provide a method of creating betel leaf extract composition has bactericidal and antiviral properties, including simple steps, low-cost, taking advantage of raw materials that are available, easy to collect, non-toxic, and environmentally friendly, but still ensure the quality and effectiveness of bactericidal and antiviral products.

This invention provides solutions to achieve the above goals.

SUMMARY OF THE INVENTION

Accordingly, an objective of the present invention is to provide a bactericidal, and antiviral composition including a betel leaf extracts/essential oils combined with at least two active ingredients plant extracts, a 4-allylpyrocatechol (APC) ingredient, and a mixing ingredients.

Another objective of the present invention is to provide a bactericidal, and antiviral composition including betel leaf extracts/essential oils combined with at least two active ingredients plant extracts, selected from the one or two or more selected plants from the following genera *Piper, Mentha, Eucalyptus, Syringa, Ocimum*.

Yet another objective of the present invention is to provide a bactericidal, and antiviral composition including betel leaf extracts/essential oils combined with at least two active ingredients plant extracts, selected from the one or two or more selected plants of the following species *Eucalyptus camaldulensis, Eucalyptus alba, Eucalyptus Tereticornis, Eucalyptus Exserta, Eucalyptus Citriodora, Eucalyptus globules, Eucalyptus grandis, Eucalyptus saligna, Eucalyptus Maidenii, Eucalyptus Urophyla, Eucalyptus brassina, Eucalyptus pellita, Eucalyptus microcorys, Mentha arvensis, Mentha piperita, Mentha longifolia*, Pennyroyal Mint, Ginger Mint (*Mentha betis gentileum, Syringa; Piper betis gentileum, Syringa*.

Another objective of the present invention is to provide a bactericidal and antiviral composition obtained from the process consisting of forming a foundation mixture by mixing betel leaf extracts/essential oils combined with at least two active ingredients plant extracts, then admixing the foundation mixture with 4-allylpyrocatechol (APC) ingredient, and the mixing ingredients having a specific predetermined percentage (%) by weight relative to the total weight of the bactericidal and antiviral composition.

Another objective of the present invention is to provide a bactericidal and antiviral composition comprises the following chemical ingredients: a eucalyptol element having 0.92%-45% by weight; a menthol element having 0.42%-15% by weight; a camphor element having 0%-10% by weight; a methyl salicylate element having 0.6%-15% by weight; an alcohol element having 3%-9% by weight; a eugenol element having 0.02%-0.1% by weight; a 4-allylpyrocatechol (APC) element having 0.5%-5% by weight; a chavibetol (CHV) element having 0.01%-1% by weight; and a 4-allylpyrocatechol acetate element having 0.01%-1%.

In view of the foregoing, another objective of the present invention is to provide a process to create antibacterial and antiviral composition includes the following steps:

i) Preparing materials, specifically determining the percentage (%) of the weight of each ingredient creating the bactericidal and antiviral composition including: (a) a betel leaf extracts/essential oils; (b) a menthol extracts/essential oils; (c) a eucalyptus extracts/essential oils; (d) a clove extract/essential oils; (e) a camphor ingredient; (f) a water paraffin ingredient; (g) an alcohol ingredient; (h) other ingredients; (i) a 4-allylpyrocatechol (APC) ingredient; and (j) a water ingredient;

wherein said other ingredients is an aroma/flavor ingredient or a skincare ingredient selected from one or more ingredients including mint, lavender, rose, lotus, cinnamon, melaleuca, basil, lemongrass, orange/mandarin/grapefruit/lemon, aloe, avocado;

wherein said betel leaf extract/essential oil and 4-allylpyrocatechol (APC) ingredient extracted from fresh or dried betel leaves crushed/chopped/or not chopped, immersed are soaked in liquid water, or solvent, or brine solution, or saturated brine solution; betel leaves are better used than old, and fresh betel leaves, controlled with a planting temperature of 24° C.-32° C. and a humidity of 70%-88%;

wherein said the 4-allylpyrocatechol (APC) ingredient including the commercial 4-allylpyrocatechol (APC) ingredient, and/or the 4-allylpyrocatechol (APC) ingredient obtained extracted from the 4-allylpyrocatechol (APC) extraction process from leaves betel; preferably the 4-allylpyrocatechol (APC) ingredient obtained extracted from the 4-allylpyrocatechol (APC) extraction process from leaves betel;

ii) mixing the ingredients in step i) in three stages:

stage 1: creating a foundation mixture by the prepared materials in the order that the betel leaf extracts/essential oils with at least two plant extracts including the menthol extracts/essential oils, the eucalyptus extracts/essential oils, and the clove extract/essential oils; all are mixed at temperatures of 25° C.-40° C., with stirring 20-40 rpm for 2-5 minutes;

stage 2: creating a homogeneous mixture by mixing a foundation mixture in stage 1 with the prepared materials in the order that the camphor ingredient, the water paraffin ingredient, the alcohol ingredient, and the water ingredient; all are mixed at temperatures of 25° C.-40° C., with stirring 40 rpm for 3-10 minutes;

stage 3: creating a base composition by mixing a homogeneous mixture with the 4-allylpyrocatechol (APC) ingredient at the temperature of 25° C.-40° C., with stirring 40 rpm for 3-10 minutes;

iii) filtering, and packing the base composition in step ii) in a vacuum at a temperature of 30° C.-40° C. to obtain the bactericidal and antiviral composition.

Another purpose of the invention is to provide an antibacterial, antiviral composition, which has four different formulas depending on the relative percentage (%) of each ingredient, which can be used for resistance bactericidal, antiviral, and deodorant.

Finally, the purpose of the invention is to provide a simple and cost-effective implementation method for creating the bactericidal and antiviral composition described above containing plant-derived virus inactivating agent in a non-irritating amount, lasts more than one hour, safe for all ages, especially children.

These and other advantages of the present invention will no doubt become obvious to those of ordinary skill in the art after having read the following detailed description of the preferred embodiments, which are illustrated in the various drawing Figures.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION OF THE INVENTION

Figure 1:
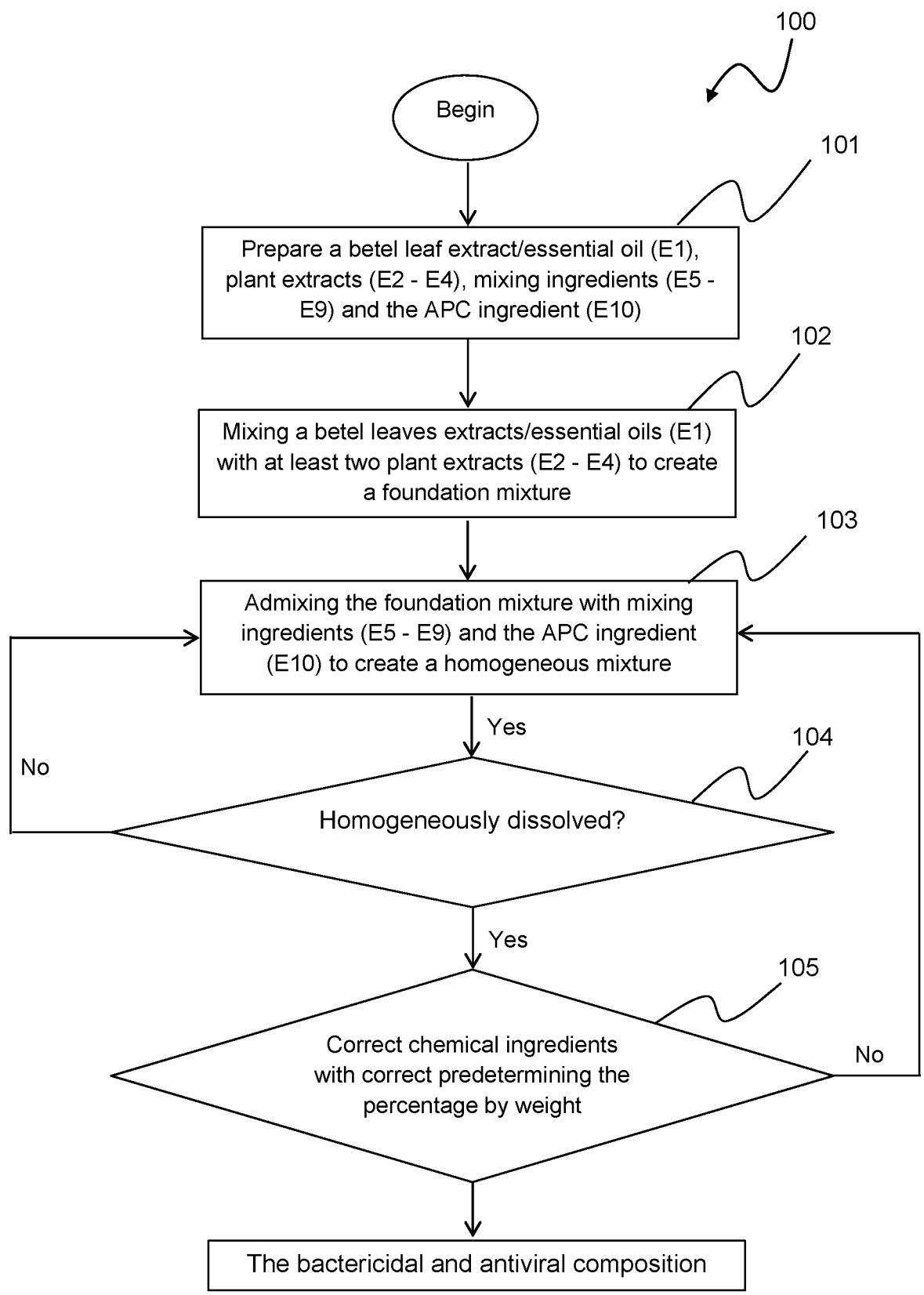
FIG. 1 is a flowchart illustrating a flowchart of a general method of manufacturing the antibacterial, antiviral composition based on the above principle in accordance with an exemplary embodiment of the present invention.

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well-known methods, procedures, components, and circuits have not been described in detail so as not to unnecessarily obscure aspects of the present invention.

According to the embodiment of the present invention, a bactericidal, and antiviral composition including betel leaf extracts/essential oils combined with at least two active ingredients plant extracts, the 4-allylpyrocatechol (APC) ingredient, and the mixing ingredients to enhance the virus inactivation ability of the composition.

As the plant extract in the present invention, an "extracts/essential oil" extracted as an aromatic substance contained in the above-mentioned plants is preferable. The essential oil in a narrow sense obtained by steam distillation from the above plants or dried materials thereof is preferably used as the "extracts/essential oil" in the present invention, but is not limited thereto. For example, oils extracted from the plants by using other methods such as extraction or expression are also included in the "extracts/essential oil" of the present invention as long as they contain essential oil components (such as aromatic substances). As other methods for extracting essential oils from plants, for example, solvent extraction (such as alcohol extraction, organic solvent extraction), oil and fat adsorption extraction (hot enfleurage or cold enfleurage), and supercritical fluid extraction are known. When the steam distillation cannot be applied because of a low essential oil content in the plant and the like, the solvent extraction is often used. Examples of the solvent used for extraction include, but are not limited to, alcohols such as ethanol, methanol, propanol, isopropanol, and butanol, and organic solvents including relatively high polarity solvents such as acetone and low polarity solvents such as hexane. The "extracts/essential oil" in the present invention may be those in which the oil obtained by the above method is further purified and concentrated by using various purification procedures such as hydrophobic or adsorptive chromatography using a support such as porous beads, silica gel, or alumina.

In the present invention and the specification of the present application, "virus inactivation" refers to removing or significantly reducing the infectivity or the growth capacity of the virus. The virus that can be inactivated by the virus inactivating agent of the present invention is not particularly limited and various viruses can be inactivating targets regardless of the genome type or the presence or absence of an envelope.

According to the embodiment of the present invention, a bactericidal and antiviral composition including betel leaf extracts/essential oils combined with at least two active ingredients plant extracts, selected from the one or two or more selected plants from the following genera *Piper, Mentha, Eucalyptus, Syringa, Ocimum.*

According to the embodiment of the present invention, a bactericidal and antiviral composition including betel leaf extracts/essential oils combined with at least two active ingredients plant extracts, selected from the one or two or more selected plants of the following species *Eucalyptus camaldulensis, Eucalyptus alba, Eucalyptus Tereticornis, Eucalyptus Exserta, Eucalyptus Citriodora, Eucalyptus globules, Eucalyptus grandis, Eucalyptus saligna, Eucalyptus Maidenii, Eucalyptus Urophyla, Eucalyptus brassina, Eucalyptus pellita, Eucalyptus microcorys, Mentha arvensis, Mentha piperita, Mentha longifolia,* Pennyroyal Mint, Ginger Mint *(Mentha betis gentileum, Syringa; Piper betis gentileum, Syringa.*

According to the embodiment of the present invention, a bactericidal and antiviral composition includes the ingredients listed in Table 1, including: a betel leaf extracts/essential oils (E1) having a first predetermined percentage (%) by weight; a menthol extracts/essential oils (E2) having a second predetermined percentage (%) by weight; an eucalyptus extracts/essential oils (E3) having a third predetermined percentage (%) by weight; a clove extract/essential oils (E4) having a fourth predetermined percentage (%) by weight; a camphor ingredient (E5) having a fifth predetermined percentage (%) by weight; a water paraffin ingredient (E6) having a sixth predetermined percentage (%) by weight; an alcohol ingredient (E7) having a seventh predetermined percentage (%) by weight; other ingredients (E8) having a eighth predetermined percentage (%) by weight; a water ingredient (E9) having a ninth predetermined percentage (%) by weight; and 4-allylpyrocatechol (APC) ingredient having a tenth predetermined percentage (%) by weight; wherein the sum of said first predetermined percentage (%) by weight to said tenth percentage (%) by weight adds up to 100% by weight of the said bactericidal and antiviral composition.

In the embodiment of the present invention, percent mass or percentage (%) by weight=(mass of solute/mass of solution)×100%. The unit of mass is usually grams. Mass percent is also known as the correct percentage by weight or w/w %. It should also be noted that the molar mass is also within the meaning of the invention. Molar mass is the total mass of all atoms in a mole of compound. Total all volume percentages add up to 100%.

Another embodiment of the invention, the percentage (%) of the weight of each ingredient creating the bactericidal and antiviral composition including: the betel leaf extracts/essential oils having 20%-45% by weight; the menthol extracts/essential oils having 10%-30% by weight; the eucalyptus extracts/essential oils having 0%-25% by weight; the clove extract/essential oils having 0%-5% by weight; the camphor ingredient having 0%-10% by weight; the water paraffin ingredient having 0%-16% by weight; the alcohol ingredient having 3%-9% by weight; the other ingredients having 0%-0.1% by weight; the 4-allylpyrocatechol (APC) ingredient having 0.5%-5% by weight; and the water ingredient.

One embodiment of the invention is now described with reference to FIG. 1. FIG. 1 illustrating a specific method of manufacturing the antibacterial, antiviral composition ("method 100") based on the above principle in accordance with an exemplary embodiment of the present invention. In particular, method 100 includes the following steps:

At step 101, all the ingredients from E1 to E10 are carefully prepared and stored in separate instruments. It should be noted that a betel leaf extracts/essential oils E1 and the APC ingredient E10 extracted from fresh or dried betel leaves crushed/chopped/or not chopped, immersed are soaked in liquid water, or solvent, or brine solution, or saturated brine solution for a long time to extract the necessary compound components from the infused betel leaves into the liquid; betel leaves are better used than old, and fresh betel leaves, controlled with a planting temperature of 24° C.-32° C. and a humidity of 70%-88%.

According to the embodiment of the present invention, the APC ingredient E10 including the commercial 4-allylpyrocatechol (APC) ingredient, and/or the 4-allylpyrocatechol (APC) ingredient obtained extracted from the 4-allylpyrocatechol (APC) extraction process from leaves betel; preferably the 4-allylpyrocatechol (APC) ingredient obtained extracted from the 4-allylpyrocatechol (APC) extraction process from leaves betel;

At step 102, a mixture of betel leaf extracts/essential oils (E1) with at least two plant extracts (E2-E4) is intended to dilute, prolong the time and increase deodorizing, bactericidal, and antiviral activity; to create a foundation mixture.

Within the scope of the present invention, the term "foundation mixture" includes the following meanings:
(a) A foundation mixture is a solution that completely dissolves the composition of the betel leaf extracts/essential oils with at least two plant extracts including the menthol extracts/essential oils, the eucalyptus extracts/essential oils, and the clove extract/essential oils having the correct percentage (%) by weight;
(b) A foundation mixture that completely dissolves the composition of soluble aromatic extracts and the composition of other supplements the correct percentage (%) by weight, does not retain any major fragrance of disinfectant bacteria, antiviral that the invention wants to mention;
(c) A foundation mixture act as a reactant, allowing the addition of ingredients to contribute their chemical and physical properties to create a new preparation;
(d) A foundation mixture chemically bonds with other complementary ingredients such as ionization reactions, covalent reactions, reducing reactions, replacement reactions, and rearrangement reactions to form a new chemical composition.

At step 103, when foundation mixture is admixed to five mixing ingredients (E5-E9) and the APC ingredient (E10) of a predetermined percentage (%) by weight listed in Table 1 below and will be discussed later. However, in an exemplary embodiment of the present invention, each type of mixing ingredients (E5 to E9) and the APC ingredient (E10) is added in a particular order. It should be noted that when the five mixing ingredients (E5-E9) and the APC ingredient (E10) are not admixed in the specific order described, the final product will not have the chemical compositions listed in Table 2 below. Therefore, the final product will not have deodorizing, bactericidal, and antiviral properties. Step 103 is performed by a magnetic stirrer. Magnetic stirrer has been known in previous art so the description of the structure and its operating principle will not be described in detail in the invention.

It is also noted that the terminology "admixed" in step 103 used in the present invention means that foundation mixture is added or reacted with or dissolved homogeneously to the plurality of mixing ingredients (E5-E9) and the APC ingredient (E10) using stirrers such as magnetic stirrers. At the same time, chemical bonds are formed between the foundation mixture and the plurality of mixing ingredients (E5-E9) and the APC ingredient (E10) include, but not limited to, addition reactions, elimination reactions, substitution reactions, tricyclic reactions, rearrangement reactions, photochemical reactions and redox reactions to form a new chemical composition.

At step 104, each time the foundation mixture is admixed to each type of mixing ingredients (E5-E9) and the APC ingredient (E10), the resulted temporary mixture. If the mixture mixing of mixing ingredients (E5 to E9) and the APC ingredient (E10) is not uniformly dissolved in the temporary mixture, step 103 is repeated with a magnetic stirrer until homogeneous conditions are reached.

At step 105, if a predetermined composition of chemical ingredients is found and/or does not have the correct percentage (%) by weight then step 103 is repeated until the correct predetermined percentage (%) by weight is achieved. Step 105 can be done by weight spectrometers and other similar devices.

Figure 2:
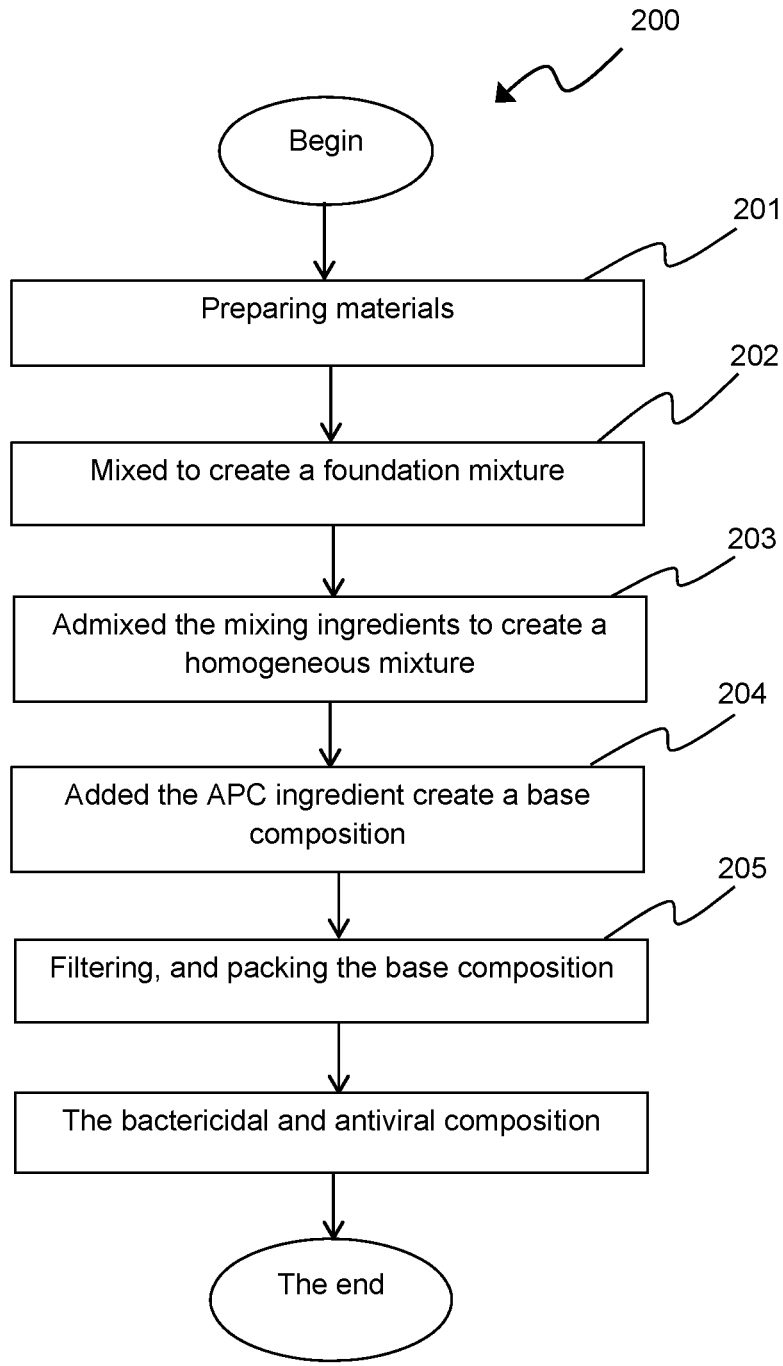
FIG. 2 is a flowchart illustrating a specific process of manufacturing the antibacterial, antiviral composition in accordance with an exemplary embodiment of the present invention.

Now referring to FIG. 2, the manufacturing process of the antibacterial, antiviral composition ("process 200") in accordance with an exemplary embodiment of the present invention, including the steps:

At step 201, preparing materials, specifically determining the percentage (%) of the weight of each ingredient creating the bactericidal and antiviral composition includes the ingredients listed in Table 1, including: a betel leaf extracts/essential oils; a menthol extracts/essential oils; a eucalyptus extracts/essential oils; a clove extract/essential oils; a camphor ingredient; a water paraffin ingredient; an alcohol ingredient; other ingredients; a 4-allylpyrocatechol (APC) ingredient; and a water ingredient; all the ingredients are carefully prepared and stored in separate instruments.

In the embodiment of the present invention, the other ingredients is an aroma/flavor ingredient or a skincare ingredient selected from one or more ingredients including mint, lavender, rose, lotus, cinnamon, melaleuca, basil, lemongrass, orange/mandarin/grapefruit/lemon, aloe, avocado.

In the embodiment of the present invention, the betel leaf extract/essential oil and the APC ingredient extracted from fresh or dried betel leaves crushed/chopped/or not chopped, immersed are soaked in liquid water, or solvent, or brine solution, or saturated brine solution; betel leaves are better used than old, and fresh betel leaves, controlled with a planting temperature of 24° C.-32° C. and a humidity of 70%-88%;

In the embodiment of the present invention, the APC ingredient is a phenolic compound of the catechol group. APC has the ability to cyclically bind with $Fe^{2+}$, has better free radical scavenging potential, so the antioxidant activity such as lipid peroxidation, free radical scavenging activity of APC will be much higher than that of chavibetol and eugenol. The APC ingredient including the commercial APC ingredient, and/or the APC ingredient obtained extracted from the APC extraction process from leaves betel; preferably the APC ingredient obtained extracted from the APC extraction process from leaves betel.

At step 202, mixing the betel leaf extracts/essential oils having a predetermined percentage (%) E1 by weight in step 201 with at least two plant extracts including the menthol extracts/essential oils, the eucalyptus extracts/essential oils, and the clove extract/essential oils having the correct percentage (%) from E2 to E4 by weight. All are mixed at temperatures of 25° C.-40° C., with stirring 20-40 rpm for 2-5 minutes; to create a foundation mixture.

According to the embodiment of the present invention, the foundation mixture of all four formulas is composed of the betel leaf extracts/essential oils having 20%-45% by weight; the menthol extracts/essential oils having 10%-30% by weight; and the clove extract/essential oils having 0%-5% by weight. Formula 1 and formula 2 creating the foundation mixture are composed of the eucalyptus extracts/essential oils having 10%-25% by weight. Formula 3 and formula 4 creating the foundation mixture are composed of the eucalyptus extracts/essential oils having 0%-10% by weight.

In another embodiment of the present invention, the foundation mixture comprises the following chemical ingredients: a eucalyptol element having 0.92%-45% by weight; a menthol element having 0.42%-15% by weight; a methyl salicylate element having 0.6%-15% by weight, a eugenol element having 0.02%-0.1% by weight; a chavibetol (CHV) element having 0.01%-1% by weight; and a 4-allylpyrocatechol acetate (APC acetate) element having 0.01%-1%.

According to the preferred embodiment of the present invention, it is preferable that the content of the eucalyptol element which is extracted fromold, and fresh betel leaves, controlled with a planting temperature of 24° C.-32° C. and a humidity of 70%-88%.

At step 203, the foundation mixture is admixed into five mixing ingredients (E5-E9) in order, including a camphor ingredient; a water paraffin ingredient, the alcohol ingredient, the other ingredients, and the water ingredient in the predetermined percentage (%) of the weight; all are mixed at temperatures of 25° C.-40° C., with stirring 40 rpm for 3-10 minutes; to create a homogeneous mixture. According to the embodiment of the present invention, each of the mixing ingredients (E5-E9) may be selected and added, one or two or more of which may be used in combination in the order with the foundation mixture.

According to the embodiment of the present invention, the homogeneous mixture of all four formulas is composed of the water paraffin ingredient having 0%-16% by weight, the alcohol ingredient having 3%-9% by weight, and the other ingredients having 0%-0.1% by weight. Formula 1 and formula 3 creating the homogeneous mixture are composed of the camphor ingredient having 5%-10% by weight. Formula 2 and formula 4 creating the homogeneous mixture are composed of the camphor ingredient having 0%-5% by weight.

At step 204, mixing the APC ingredient in the predetermined percentage (%) of the weight into the homogeneous mixture at the temperature of 25° C.-40° C., with stirring 40 rpm for 3-10 minutes; to create a base composition. The base composition of the present invention preferably contains essential oils in combination with mixing ingredients (E5-E9) and the APC ingredient (E10) so that the content of APC contained in the base composition is 0.5% by weight or more based on the total amount of the virus inactivating agent. If the content of APC is less than 0.5% by weight, a sufficient virus inactivation effect cannot be obtained.

The upper limit of the content of APC is not particularly limited, but is typically 5% by mass or less, preferably 4% by mass or less, 3.5% by mass or less, or 2% by mass or less, or 1% by mass or less. According to the embodiment of the present invention, the base composition of all four formulas is composed of the APC ingredient having 0.5%-5% by weight.

Finally, at step 205, filtering, and packing the base composition in step 204 in a vacuum at a temperature of 30° C.-40° C. to obtain the bactericidal and antiviral composition.

According to the embodiment of the present invention, the bactericidal and antiviral composition obtained from process 200 comprises the following chemical ingredients: a eucalyptol element having 0.92%-45% by weight; a menthol element having 0.42%-15% by weight; a camphor element having 0%-10% by weight; a methyl salicylate element having 0.6%-15% by weight; an alcohol element having 3%-9% by weight; a eugenol element having 0.02%-0.1% by weight; a 4-allylpyrocatechol (APC) element having 0.5%-5% by weight; a chavibetol (CHV) element having 0.01%-1% by weight; and a 4-allylpyrocatechol acetate (APC acetate) element having 0.01%-1%.

TABLE 1

Mixed components of the bactericidal, and antiviral composition

| Note | Name of | Percentage (%) formulation | | | |
|---|---|---|---|---|---|
| | | Formula 1 | Formula 2 | Formula 3 | Formula 4 |
| E1 | A betel leaf extracts/ essential oils | 20%-45% | 20%-45% | 20%-45% | 20%-45% |
| E2 | A menthol extracts/ essential oils | 10%-30% | 10%-30% | 10%-30% | 10%-30% |
| E3 | A eucalyptus extracts/ essential oils | 10%-25% | 10%-25% | 0%-10% | 0%-10% |
| E4 | A clove extract/ essential oils | 0%-5% | 0%-5% | 0%-5% | 0%-5% |
| E5 | Camphor | 5%-10% | 0%-5% | 5%-10% | 0%-5% |
| E6 | Water paraffin | 0%-16% | 0%-16% | 0%-16% | 0%-16% |
| E7 | Alcohol | 3%-9% | 3%-9% | 3%-9% | 3%-9% |
| E8 | Other ingredients | 0%-0.1% | 0%-0.1% | 0%-0.1% | 0%-0.1% |
| E9 | Water | rest | rest | rest | rest |
| E10 | APC | 0.5%-5% | 0.5%-5% | 0.5%-5% | 0.5%-5% |

TABLE 2

Chemical ingredients of the bactericidal and antiviral composition

| No. | Chemical ingredients | W/W (%) |
|---|---|---|
| 1 | Eucalyptol | 0.92%-45% |
| 2 | Menthol | 0.42%-15% |
| 3 | Methyl salicylate | 0.6%-15% |
| 4 | Eugenol | 0.02%-0.1% |
| 5 | Camphor | 0%-10% |
| 6 | Chavibetol (CHV) | 0.01%-1% |
| 7 | Alcohol | 3%-9% |
| 8 | 4-allylpyrocatechol (APC) | 0.5%-5% |
| | 4-allylpyrocatechol acetate (APC acetate) | 0.01%-1% |

The form of the bactericidal, and antiviral composition of the present invention may be a solution, a cream, a paste, a gel, a foam, a solid, or a powder, depending on the dosage form thereof.

The composition of the present invention contains plant extracts, non-toxic, safe to use, and limits cross-infection from bacteria and viruses through the respiratory tract; 99.99% bactericidal efficiency, has antiviral ability in general and contributes to the prevention of coronavirus in particular. Contributing to diversifying products, promoting the strengths of medicinal plants in general, and *piper betel* L. in particular.

In addition, the results of analysis on bactericidal and safety of the bactericidal, and antiviral composition were created by method 100 and process 200 were tested on toxicity. The toxicity (0.01 mL/20 body weight, applied to the skin on the back for 30 days) in mouse did not affect the erythrocyte parameters, AST, ALT, and creatinine. The composition increased the number of white blood cells, but did not affect the percentage of MID cells, monocytes, Granulocytes compared with the control batch using the solvent. At the same time, there were no differences in the microstructural characteristics of the liver and kidneys of the mouse when using the composition compared to the control using the solvent.

The bactericidal, and antiviral composition of the present invention may be to kill bacteria and viruses is tested for biological activity including cytotoxicity test, antioxidant test by DPPH free radical scavenging and resistance to lipid peroxidation, and antimicrobial activity tests are listed in Table 3 below.

TABLE 3

Results of biological activity testing of the bactericidal, and antiviral composition according to the embodiment of the present invention

| No. | Biological activity testing | Result |
| --- | --- | --- |
| 1 | Lung cancer cell cytotoxicity rate (NCI-H460) | (+) |
| 2 | DPPH free radical scavenging | (+) |
| 3 | Resistance to lipid peroxidation | (+) |
| 4 | Antimicrobial activity | *Staphylococcus aureus, Escherichia coli, Candida albicans, Pseudomonas aeruginosa, Bacillus subtillis* | wherein, (+) is a positive sample, having the lung cancer cell cytotoxicity rate (NCI-H460)/DPPH free radical scavenging/lipid Resistance to lipid peroxidation greater than 50%.

According to the embodiment of the present invention, the production method produces 1 liter of the bactericidal, and antiviral composition including five examples listed in Table 4 below.

TABLE 4

Mixed components of the bactericidal, and antiviral composition in five examples according to the embodiment of the present invention

| Name of | Example 1 | Example 2 | Example 3 | Example 4 | Example 5 |
| --- | --- | --- | --- | --- | --- |
| A betel leaf extracts/ essential oils | 0.3 | 0.3 | 0.2 | 0.2 | 0.3 |
| A menthol extracts/ essential oils | 0.1 | 0.2 | 0.1 | 0.1 | 0.1 |
| A eucalyptus extracts/ essential oils | 0 | 0 | 0.1 | 0 | 0 |
| A clove extract/ essential oils | 0 | 0.0006 | 0.0006 | 0 | 0 |
| Camphor | 0.1 | 0.1 | 0.05 | 0 | 0 |
| Water paraffin | 0.12 | 0.12 | 0.13 | 0 | 0 |

TABLE 4-continued

Mixed components of the bactericidal, and antiviral composition in five examples according to the embodiment of the present invention

| Name of | Example 1 | Example 2 | Example 3 | Example 4 | Example 5 |
| --- | --- | --- | --- | --- | --- |
| Alcohol | 0.05 | 0.05 | 0.05 | 0.05 | 0.09 |
| Other ingredients | 0.0005 | 0.0005 | 0.0005 | 0.0001 | 0.0001 |
| APC | 0.035 | 0.035 | 0.035 | 0.0005 | 0.0005 |
| Water | rest | rest | rest | rest | rest |

According to some example embodiment mentioned in Table 4, the bactericidal and antiviral composition according to examples 1, 2 and 3 are liquid composition with a characteristic color and aroma for external use or for the treatment of eye-related diseases with sauna measures. Composition according to example 4 is applied in the form of a palate spray; and composition according to example 5 is applied antiseptic to the skin and sprayed directly on products that need to be disinfected and antiviral.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, element components, and/or groups thereof.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order, or steps may be added, deleted, or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A process of manufacturing a bactericidal, and antiviral composition, comprising steps performed in the following specific order:
    i) Preparing materials and determining the percentage (%) by weight of the ingredients including:
    (a) a betel leaf extracts/essential oils; (b) a menthol extracts/essential oils; (c) an eucalyptus extracts/essential oils; (d) a clove extract/essential oils; (e) a camphor ingredient; (f) a water paraffin ingredient; (g) an alcohol ingredient; (h) other ingredients; (i) a 4-allylpyrocatechol (APC) ingredient; and (j) a water ingredient;
    wherein said the betel leaf extract/essential oil and the 4-allylpyrocatechol (APC) ingredient extracted from fresh betel leaves are soaked in liquid water, solvent, brine solution, or saturated brine solution; wherein fresh betel leaves controlled with a temperature of 24° C.-32° C. and a humidity of 70%-88%;
    wherein said the 4-allylpyrocatechol (APC) ingredient including the commercial 4-allylpyrocatechol (APC) ingredient, and/or the 4-allylpyrocatechol (APC) ingredient obtained from the 4-allylpyrocatechol (APC) extraction process from betel leaves;
    wherein said the other ingredients including an aroma/flavor ingredient or a skincare ingredient selected from one or more ingredients including mint, lavender, rose, lotus, cinnamon, melaleuca, basil, lemongrass, orange/mandarin/grapefruit/lemon, aloe, avocado;
    ii) mixing the ingredients in step i) in three stages:
    stage 1: preparing materials for a foundation mixture by mixing the betel leaf extracts/essential oils with plant extracts the menthol extracts/essential oils, the eucalyptus extracts/essential oils, and the clove extract/essential oils; all are mixed at temperatures of 25° C.-40° C., and stirring at 20-40 rpm for 2-5 minutes;
    stage 2: creating a homogeneous mixture by mixing the foundation mixture with the camphor, the water paraffin, the alcohol, the other ingredients and water; all are mixed at temperatures of 25° C.-40° C., with stirring 40 rpm for 3-10 minutes;
    stage 3: creating a base composition by mixing the homogeneous mixture with the 4-allylpyrocatechol (APC) at the temperature of 25° C.-40° C., and stirring at 40 rpm for 3-10 minutes;
    iii) filtering, and packing the base composition in step ii) in a vacuum at a temperature of 30° C.-40° C. to obtain the bactericidal and antiviral composition.

2. The process of claim 1 wherein the bacterial and antiviral activity depend on weight percentages of ingredients (a)-(j) in a first, a second, a third, and a fourth formula, wherein the third formula is more potent than the first formula; and the fourth formula is more potent than the second formula.

3. The process of claim 2 wherein the first formula comprises:
    (a) the betel leaf extracts/essential oils having 20%-45% by weight;
    (b) the menthol extracts/essential oils having 10%-30% by weight;
    (c) the eucalyptus extracts/essential oils having 10%-25% by weight;
    (d) the clove extract/essential oils having 0.0006%-5% by weight;
    (e) the camphor ingredient having 5%-10% by weight;
    (f) the water paraffin ingredient having 10%-16% by weight;
    (g) the alcohol ingredient having 3%-9% by weight;
    (h) the other ingredients having 0.0001%-0.1% by weight;
    (i) the 4-allylpyrocatechol (APC) ingredient having 0.5%-5% by weight; and
    (j) the remainder is the water ingredient.

4. The process of claim 3 wherein the second formula comprises:
    (a) the betel leaf extracts/essential oils having 20%-45% by weight;
    (b) the menthol extracts/essential oils having 10%-30% by weight;
    (c) the eucalyptus extracts/essential oils having 10%-25% by weight;
    (d) the clove extract/essential oils having 0.0006%-5% by weight;
    (e) the camphor ingredient having 0.05%-5% by weight;
    (f) the water paraffin ingredient having 10%-16% by weight;
    (g) the alcohol ingredient having 3%-9% by weight;
    (h) the other ingredients having 0.0001%-0.1% by weight;
    (i) the 4-allylpyrocatechol (APC) ingredient having 0.5%-5% by weight; and
    (j) the remainder is the water ingredient.

5. The process of claim 2 wherein the third formula comprises:
    (a) the betel leaf extracts/essential oils having 20%-45% by weight;
    (b) the menthol extracts/essential oils having 10%-30% by weight;
    (c) the eucalyptus extracts/essential oils having 0.02%-10% by weight;
    (d) the clove extract/essential oils having 0.0006%-5% by weight;
    (e) the camphor ingredient having 5%-10% by weight;
    (f) the water paraffin ingredient having 10%-16% by weight;
    (g) the alcohol ingredient having 3%-9% by weight;
    (h) the other ingredients having 0.0001%-0.1% by weight;
    (i) the 4-allylpyrocatechol (APC) ingredient having 0.5%-5% by weight; and
    (j) the remainder is the water ingredient.

6. The process of claim 5 wherein the fourth formula comprises:
    (a) the betel leaf extracts/essential oils having 20%-45% by weight;
    (b) the menthol extracts/essential oils having 10%-30% by weight;
    (c) the eucalyptus extracts/essential oils having 0.02%-10% by weight;
    (d) the clove extract/essential oils having 0.0006%-5% by weight;
    (e) the camphor ingredient having 0.05%-5% by weight;
    (f) the water paraffin ingredient having 10%-16% by weight;
    (g) the alcohol ingredient having 3%-9% by weight;
    (h) the other ingredients having 0.0001%-0.1% by weight;
    (i) the 4-allylpyrocatechol (APC) ingredient having 0.5%-5% by weight; and
    (j) the remainder is the water ingredient.

* * * * *